United States Patent [19]

Kahney et al.

[11] 4,000,178

[45] Dec. 28, 1976

[54] PARAFFIN AMMOXIDATION PROCESS

[75] Inventors: Ronald H. Kahney, Oakland; Talmage D. McMinn, Jr., St. Louis, both of Mo.

[73] Assignee: Monsanto Company, St. Louis, Mo.

[22] Filed: Sept. 19, 1975

[21] Appl. No.: 615,153

[52] U.S. Cl. ............................................ 260/465.3
[51] Int. Cl.² .................................... C07C 120/14
[58] Field of Search ................................ 260/465.3

[56] References Cited

UNITED STATES PATENTS

| | | | |
|---|---|---|---|
| 2,518,295 | 8/1950 | Denton et al. | 260/465.3 X |
| 3,478,082 | 11/1969 | Huibers | 260/465.3 |
| 3,639,103 | 2/1972 | Sheely | 260/465.3 X |
| 3,652,638 | 3/1972 | Riegel et al. | 260/465.3 |
| 3,699,147 | 10/1972 | Huibers et al. | 260/465.3 X |
| 3,816,506 | 6/1974 | Taylor | 260/465.3 |
| 3,839,398 | 10/1974 | Leto et al. | 260/465.9 X |
| 3,925,447 | 12/1975 | Gelbein | 260/465.3 X |

FOREIGN PATENTS OR APPLICATIONS

| | | | |
|---|---|---|---|
| 1,194,855 | 6/1970 | United Kingdom | 260/465.3 |
| 1,265,786 | 3/1972 | United Kingdom | 260/465.3 |

*Primary Examiner*—Joseph Paul Brust
*Attorney, Agent, or Firm*—J. C. Logomasini; P. L. Passley; N. E. Willis

[57] ABSTRACT

Method of ammoxidizing paraffin hydrocarbons to unsaturated nitriles in a transported bed reactor at a temperature of from 350° to 550° C. using a catalyst comprising antimony and uranium.

10 Claims, 1 Drawing Figure

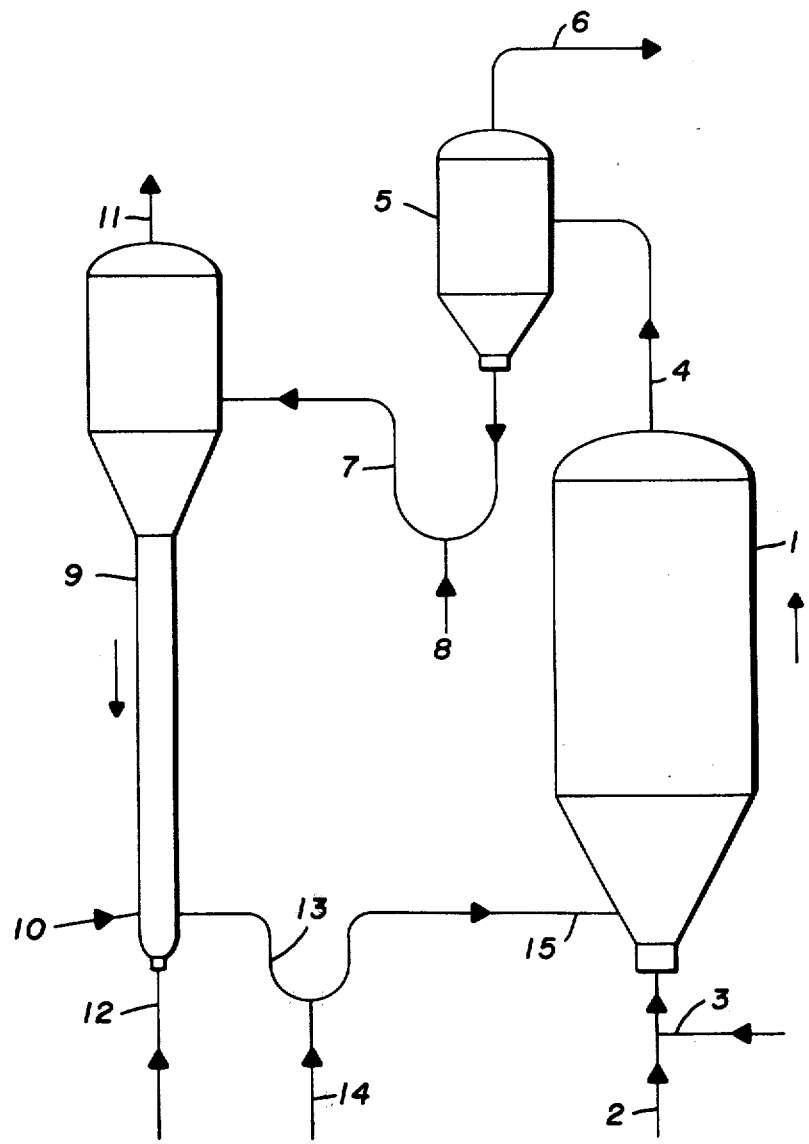

PARAFFIN AMMOXIDATION PROCESS

BACKGROUND OF THE INVENTION

This invention relates to the ammoxidation of paraffin hydrocarbons to unsaturated nitriles, particularly alpha, beta-unsaturated nitriles.

The value of alpha, beta-unsaturated nitriles is generally well recognized with acrylonitrile being among the most valuable monomers available to the polymer industry for producing useful polymeric products. Acrylonitrile is useful in the preparation of synthetic fibers, synthetic rubbers and other useful plastic products.

Many processes, catalytic and non-catalytic, are known and practised for the manufacture of alpha, beta-unsaturated nitriles. A generally practised catalytic ammoxidation process is performed in the vapor phase in the presence of a catalyst. For the production of acrylonitrile, propylene is the olefin reactant.

Propane is a source of carbon which is lower in cost than propylene or any other material useful as a starting material in the manufacture of acrylonitrile. Therefore, it is readily recognized that a feasible process for producing acrylonitrile directly from propane would be highly desirable.

Although some art has developed on the ammoxidation of propane to form acrylonitrile, a commercially feasible process has not heretofore been reported because the ultimate yield of acrylonitrile obtained from propane is relatively low. For example, U.S. Pat. No. 3,365,482 discloses the use of molybdenum oxide or tungsten oxide as catalysts for the conversion of propane to acrylonitrile. However, it is observed from this reference that the ultimate yield of acrylonitrile, based on propane converted, is low.

A process applied to the ammoxidation of propylene or isobutylene to acrylonitrile or methacrylonitrile respectively is described in U.S. Pat. No. 3,478,082. This process comprise heating a fluidized ammoxidation catalyst in the presence of a gas comprising molecular oxygen to yield, in a first or oxygenation zone, the catalyst in oxygenated form transporting the oxygenated catalyst therefrom by fluidized solids transportation techniques to a second or reaction zone contacting the ocygenated catalyst in a fluidized state with an unsaturated hydrocarbon and ammonia in the second or reaction zone to yield the nitrile product, and recycling the oxygen-depleted catalyst back to the first, or oxygenation zone to complete the cycle and reoxygenate the catalyst. This type of operation is hereinafter referred to as a transported bed reaction. However, contrary to the disclosure in that specification, it has now been found that transported bed reaction processes can be applied to the ammoxidation of saturated hydrocarbons of the paraffin series to yield alpha, beta-unsaturated nitriles providing a suitable catalyst is used.

In U.S. Pat. No. 839,398 a modified form of transported bed reactor is used to form $V_2O_4$ which is then used to ammoxidize various hydrocarbons (through paraffin hydrocarbons are one of the few group of hydrocarbons not specified). The catalyst used is $V_2O_4$ as opposed to the $V_2O_5$ of the prior art and this is the nub of the invention since it is said to reduce by-product incidence.

Another reactor in which the catalyst is cycled is disclosed in U.S. Pat. No. 3,639,103 but the cycling is in effect between stratified zones in the same reactor and such a configuration confers few of the advantages of a genuine transported bed reactor such as is used in the present invention. Moreover, the invention does not address itself to the problem of catalyst stability under oxidation/reduction cycle conditions nor to the ammoxidation of paraffin hydrocarbons but is confined to disclosure of a novel type of fluidized bed (as opposed to transported bed)reactor.

Moreover, not all catalysts which are effective in the ammoxidation of hydrocarbons to nitriles can be used in transported bed reactors since the nature of the reactor demands that they be stable to repeated oxidation/reduction cycles at elevated reaction temperatures. Thus, a suitable catalyst is one which is capable of efficiently ammoxidizing saturated hydrocarbons and which is capable of operating under repeated oxidation/reduction cycle conditions at elevated temperatures. One solution to this problem is set forth in U.S. Pat. No. 3,652,638 in which instead of fluidized catalyst bed, a catalyst is used which comprises a molten metal oxyhalide which gives up its oxygen and is in a separate zone reconverted to the oxyhalide. This does not, of course, utilize the principles of a fluidized bed reactor or a transported bed reactor but it does illustrate an alternative solution to the problem of finding a catalyst stable under reaction conditions which comprise repeated oxidation/reduction cycles at high tempertures.

A suitable catalyst has now been found that can be used in conjunction with transported catalyst bed technology to produce unsaturated nitriles from paraffinic hydrocarbons more efficiently that the hitherto-known processes.

The present invention has its objects, the provision of an improved vapor phase process for the production of alpha, beta-unsaturated nitriles by ammoxidation of paraffin hydrocarbons. A further object is to provide a transported catalyst bed process for the ammoxidation of paraffin hydrocarbons to alpha, beta-unsaturated nitriles and more specifically for the conversion of propane and isobutane to acrylonitrile and methacrylonitrile respectively.

Other objects and advantages will become apparent to the skilled reader upon study of the disclosures contained herein and the appended claims.

The present invention provides a process for the ammoxidation of a paraffin hydrocarbon to an unsaturated nitrile which comprises reacting a paraffin hydrocarbon with ammonia and oxygen at a temperature of from 350° to 550° C in the presence of a catalyst having the empirical formula $Sb_a\ U_b\ Fe_c\ W_d\ O_3$ wherein $a$ is 1 to 10, $b$ is 0.01 to 1, $c$ is 0 to 1, $d$ is 0 to 0.1 and $e$ is a number chosen to satisfy the valencies of the other elements in the oxygenation states in which they appear characterized in that the catalyst has previously been oxygenated by heating in a molecular-oxygen containing gas, and the oxygen required by the ammoxidation reaction is provided entirely by the oxygenated catalyst.

The process of the invention is particularly useful when operated in conjunction with a transported bed reactor and the following description will be related to such a reactor for greater clarity.

Thus a specific preferred embodiment of the present invention comprises a process for the ammoxidation of a paraffin hydrocarbon to an unsaturated nitrile which comprises:

a. passing a molecular oxygen-containing gas through a fluidized bed of a catalyst in an oxygenation zone, said catalyst having the empirical formula $Sb_aU_b Fe_cW_dO_e$, wherein $a$ is 1 to 10, bis 0.01 to 1, $c$ is 0 to 1, $d$ is 0 to 0.1 and $e$ is a number chosen to satisfy the valencies of the other elements in the oxidation states in which they appear, so as to oxygenate the catalyst;

b. continuously forwarding oxygenated catalyst in a fluidized state to a reaction zone and, in said reaction zone, contacting said oxygenated catalyst in the fluidized state with a paraffin hydrocarbon and ammonia such that the paraffin hydrocarbon and ammonia react with oxygen from the oxygenated catalyst, at a temperature of from 350° to 550° C to produce the unsaturated nitrile, the oxygenated catalyst providing the only source of oxygen introduced into the reaction zone; and c. continuously removing catalyst from which oxygen has been removed from the reaction zone and transporting it in a fluidized state to the oxygenation zone.

The process of the invention is particularly effective in the production of acrylonitrile and methacrylonitrile from propane and isobutane respectively.

This type of process has several advantages relative to other ammoxidation processes for making nitriles. A major advantage is that it allows higher selectivities to be realized. Since no gas phase oxygen is added to the ammoxidation zone, gas phase side reactions with oxygen are minimized and catalytic reactions are favored. Also, higher selectivities are realized since the solids are not circulating within the reaction zone as in a fluid bed but moving more closely to plug flow as they pass through the reaction zone and backmixing of the gas is therefore minimized.

Another advantage is that the reaction products are much more concentrated than with the conventional process. Since the oxygen is fed to the reaction zone as part of the circulating solid catalyst instead of as air, the nitrogen that comprises the major portion of the air is not present to dilute the reaction zone off gases. This greatly decreases the size of units required to achieve separation of product from unreacted gases and makes simpler processing possible.

A third advantage is the safety of this system. There are no places in the apparatus where explosive mixtures of hydrocarbons and oxygen are present. Thus, much higher concentrations of hydrocarbons can be safely utilized than is the case where the paraffin is contacted with the catalyst in admixture with oxygen.

Yet another advantage lies in the option of using halogen promoters in the substantial absence of gas phase oxygen thus reducing the incidence of competing reactions affecting the activity of the promoter and potentially liberating corrosive halogen compounds.

The catalyst used in the process of the invention is one that can exist in a oxygenated form and is stable to repeated cycles in which oxygen is added and removed from the catalyst. While the catalyst forms have been characterized as "oxygenated" and "oxygen-depleted" it is not to be assumed that the oxygen is necessarily present in chemically combined form. While this is not excluded the major part of the oxygen taken up is usually adsorbed on the catalyst surface or even trapped within the catalyst structure. All such forms are understood to be embraced by the term "oxygenated" as used herein.

The active components of the catalyst are antimony and uranium and while these usually exist in the form of separate simple oxides, it is possible to have them present as complex oxides. The catalyst may contain other components which modify the activity of the catalyst such as iron and tungsten. In many cases the presence of iron and tungsten is desirable since, as is demonstrated in the Examples, replacing part of the uranium by iron and tungsten results in increased selectivity to the desired acrylonitrile product. These additional components too may be in the form of separate oxides or in the form of complex compounds with one or more of the other components and oxygen.

These include the catalysts described in U.S. Pat. Nos. 3,198,750 and 3,886,096.

Catalysts useful in the present invention have the empirical formula $Sb_{1-10}U_{0.01-1}Fe_{0-1}W_{0-0.1}O_y$ wherein $y$ is the number of oxygen atoms required to satisfy the valency states of the antimony, uranium, iron and tungsten.

The catalyst can be employed without support, and will display excellent activity. It is usual however in any fluidized catalyst bed that the active components be combined with a support, and preferably at least 5% up to about 90% and more preferably 5 to 50%, of the supporting compound by weight of the entire composition is employed in this event. Any known support materials can be used, such as, for example, silica, alumina, zirconia, alundum, silicon carbide, alumina-silica, and the inorganic phosphates, silicates, aluminates, borates and carbonates stable under the reaction conditions to be encountered in the use of the catalyst.

The ammoxidation reaction can conveniently be conducted at temperatures of, for example, 350° to 550° C but the preferred reaction temperatures are in the range of 450° to 525° C and most suitably 470° to 510° C.

The reaction is preferably conducted at substantially atmospheric pressures though higher pressures can be used if desired. However, since the reaction proceeds satisfactorily at atmospheric pressures the advantages of working at higher pressures are not generally such as to justify the expense of the high pressure equipment involved.

Since the major factor influencing the rate of conversion of the paraffin to nitrile is the amount of oxygen available from the catalyst, the conversion rate is largely independent of the partial pressures of the ammonia and paraffin fed to the reaction zone. It can be appreciated, therefore, that the rate-determining factor is the rate at which the catalyst can be recycled to the reaction zone after oxygenation. The provision of substantially all the oxygen required by the reaction through the oxygenated catalyst is not a disadvantage in that it results in a higher selectivity towards the desired nitrile product than would be the case if the available oxygen were in greater supply as in the case in processes where a gaseous hydrocarbon/oxygen mixture is reacted. Generally, the amount of available oxygen carried by the oxygenated catalyst is up to 1% and more generally from 0.1 to 0.8% and preferably 0.2 to 0.6% by weight of the active catalytic components of the catalyst.

While, as indicated above, the partial pressures of paraffin and ammonia are not rate-determining factors, it is generally preferred that the reactants be present in proportions that differ by less than 20% and preferably less than 5% by volume.

The catalyst is oxygenated or reoxygenated by heating it in the presence of a regenerator gas comprising molecular oxygen. This can be pure oxygen but more usually it is air or a mixture of gases comprising oxygen and other inert gases such as nitrogen, helium or neon.

The temperature at which the catalyst is oxygenated is conveniently that at which the ammoxidation reaction is conducted but higher or lower temperatures within the preferred reaction zone temperatures can be used if desired.

In general, it is found preferable to arrange that the catalyst residence time in the oxygenation zone be longer than that in the reaction zone perhaps by a factor of two or more such as for example 2 to 3. This can easily be achieved by, for example, adjusting the relative lengths of the zones where these zones have identical cross-sections.

The paraffin hydrocarbons to which the process of the invention most suitably applies are those comprising 3 to 5 carbon atoms such as propane, butane, isobutane, pentane and iso-pentane. The main utility of the invention, however, lies in the production of acrylonitrile and methacrylonitrile from propane and isobutane respectively.

A halogen promoter may be employed in the process of this invention. The halogen can be introduced into the reaction in any suitable manner. For example, the halogen may be introduced along with the paraffin hydrocarbon and ammonia as elemental halogen or, better, as a volatile halogen-containing compound. Alternatively, but less preferably, the catalyst can be treated in the oxygenation zone with the halogen promoter. Any halogen can be used, but at the present, bromine is the preferred halogen. Suitable volatile halogen-containing compounds are the halo-alkanes having up to 3 carbon atoms, Examples are $CH_3Br$, $CH_3Cl$, $CH_3I$, $CH_3F$, $CH_2Br_2$, $CH_2Cl_2$, $CHF_3$, $CHI_3$, $CBr_4$, $CCl_4$, $C_2H_5Cl$, $C_2H_5F$, $C_2H_4Br_2$, $C_2H_4I_2$, $C_2H_3Br_3$, $C_2H_3I_3$, $C_2H_2Br_4$, $C_2HCL_5$, $C_2Br_6$, $C_3H_7I$, $C_3H_7Br$, $C_3H_6Cl_2$, $C_3H_5Br_3$, $C_3H_5Cl_3$, $C_3H_2Br_6$, $C_3HCl_7$ and the like. The ammonium and hydrogen halides such as ammonium bromide, chloride and iodide and hydrogen fluoride, chloride and bromide can also be used with advantage. Elemental bromine is a further available option. When treating the catalyst with the halogen, a metal halide, such as the halides of lead, iron, aluminum, zinc and the like, or a non-metal halide such as an ammonium halide can be used. Generally speaking, regardless of the means of introducing the halogen promoter, the promoter will be employed in a mole ratio of from 0.00005 to 0.10 and preferably from 0.005 to 0.05 mole of halogen (measured as $X_2$ where X is flourine, chlorine, bromine or iodine) per mole of hydrocarbon used.

A suitable apparatus for operating the process of the invention is illustrated in the Drawing in which a reaction zone, 1, has a feed line, 2, through which reaction zone feed gases are fed to the bottom of the zone and there is provided a line, 3, through which, if desired, a promoter can be introduced into the feed gases. From the top of the reaction zone, an outflow line, 4, communicates with a separation chamber, 5, in which catalyst is separated from the product gas flow which exits overhead through product line, 6. The separated catalyst solid passes from the separation chamber through a first seal zone, 7, in which the seal is maintained by seal gas entering through first seal gas line, 8. Catalyst is then transported to the top end of an oxygenation zone, 9, in which it is contacted with an oxygenation gas entering through line, 10, at the base of the zone. Excess oxygenation gas along with seal gas exits the oxygenation zone overhead through vent line, 11. Seal gas enters the base of the oxygenation zone through an upper seal gas line, 12, and advances the oxygenated catalyst through a second seal zone, 13, which maintains the seal and keeps the catalyst in the fluidized state in co-operation with further seal gas introduced through a lower seal gas line, 14. Thereafter, the oxygenated catalyst is passed through line, 15, into the base of the reaction zone, 1.

In operation, the apparatus operates by maintaining a flow of catalyst from the reaction zone to the oxygenation zone and back to the reaction zone by a combination of the pressure difference in the oxygenation and reaction zones and the drag exerted on the solids by the flowing gases. This can be done, for example, by providing that the two columns of catalyst have different heights, thus creating a difference in pressure at the bottom of the reactor which is dissipated as kinetic energy of the moving catalyst. In the reaction zone, the oxygenated catalyst is contacted with a paraffin/ammonia reaction mixture which also helps to keep the catalyst moving in the fluidized state up through the zone and into the separator zone from which product gases are led off and catalyst passes into a first seal zone into which a seal gas such as nitrogen is fed to serve the dual function of keeping the catalyst moving towards the oxygenation zone and to prevent any back flow of oxygenation gas to the reaction zone. The catalyst passes from the first seal zone into the top end of an oxygenated zone where it meets a counter-current flow of an oxygenation gas comprising molecular oxygen. Excess oxygenation gas and seal gas are led off at the top of the oxygenation zone and the catalyst flows in the fluidized state down to the bottom from which it is led off through a second seal zone separating the reaction zone from the oxygenation zone by means of an upper seal gas (for example, nitrogen) flow at the base of the oxygenation zone and a lower seal gas flow intermediate between the oxygenation and reaction zones. The seal gas flow in the second seal zone also serves to forward the catalyst to the base of the reaction zone.

EXAMPLES

The following Examples which demonstrate the application of the process of the invention to the conversion of propane and isobutane to acrylonitrile and methacrylonitrile respectively, are illustrative of the process of the invention but are not considered as limiting the scope or application thereof. The apparatus used in Examples 1 to 4 and 9 and 10, and the manner in which it operates is substantially as described above with reference to the Drawing.

In more specific detail, the apparatus used comprises a cylindrical reaction zone having a length of 45 cm, an outside diameter of 25 mm and an interval volume of 165 cc; and an oxygenation zone having a length of 64 cm, an outside diameter of 41 mm and an internal volume of 692 cc. The outside diameter of the seal zones between the reaction and oxygenation zones is 18 mm.

The reactor dimensions and the gas flow rates specified in the Examples are such that the catalyst particles move through reactor and oxygenation zones along with the gases with which they are in contact in a fluidized state. The initial catalyst charge in each case was about 800 grams.

In the transported bed reactor the reactant gases were in contact with catalyst in the reaction zone for a period of 7 seconds. The catalyst stayed in the reaction zone a total of 14 seconds and in the oxygenation zone about 30 seconds.

Examples 5 to 8 and comparative experiments $C_1$ to $C_3$ were carried out in an apparatus simulating a transported bed reactor that comprised a 7 cm × 11 mm O.D. pyrex tube containing a fixed bed of approximately 7.5 grams of catalyst. The tube was provided with means for passing through the catalyst bed either an oxygenation gas or a paraffin/ammonia mixture. The reported results were obtained by cycling the flow through the reactor such that oxygenation gas was used to oxygenate the catalyst and then this flow was shut off and replaced by reactant flow. This constituted one cycle, and the cycles reported represent the number of time the catalyst was oxygenated and then used in the ammoxidation reaction.

In each case, in the reaction phase of the cycle lasting about 15 seconds, a mixture of 12 cc of propane, 12 cc of ammonia and 7.6 cc of 0.5% methyl bromide were passed through the catalyst at a temperature of 500° C and approximately atmospheric pressure. This was followed by a purge of 35 cc of helium and 0.5 cc of ammonia lasting 15 seconds. During the oxygenation phase, 29 cc of air were passed over the catalyst over a period of 30 seconds. This was succeeded by a purge exactly as before.

Examples 1 to 4 (Table 1) and 9 and 10 illustrate the conversion, selectivity and yield from a single pass of reactants through the reaction zone, and Examples 5 to 8 (Table 2) illustrate the conversion and selectivity to acrylonitrile of a range of catalysts of different compositions after being cycled in the manner described above, 100, 200 and 1,000 times in the apparatus simulating the transported bed reactor.

Comparative Experiments ($C_1$–$C_3$ on Table 2) indicate the relatively poor performance of a catalyst containing no uranium.

TABLE 1

| Ex. | Hydrocarbon used and Catalyst | GAS FLOW RATES IN CC (S.T.P.)/Min | | | | | | | Temp. in Reactor ° C. | Press. in Reactor | Hydrocarbon Conv. | Select. to nitrile | Single pass Nitrile Yield |
|---|---|---|---|---|---|---|---|---|---|---|---|---|---|
| | | Hydrocarbon | Ammonia | Air to Regenerator Z. | 0.5% $CH_3Br$ in $N_2$ | SEAL GAS (HELIUM) | | | | | | | |
| | | | | | | 1st Seal Zone | 2nd S. Zone Upper | 2nd S. Zone Lower | | | | | |
| 1 | Propane $Sb_{4.5}U_1$ | 80 | 100 | 600 | 100 | 65 | 250 | 118 | 488 | atm. | 44.7 | 70.4 | 31.5 |
| 2 | Propane $Sb_rFe_1U_1W_{0.12}$ | 80 | 100 | 600 | 64 | 250 | 250 | 120 | 480 | atm. | 40.8 | 82.2 | 33.5 |
| 3 | Isobutane $Sb_{4.5}U_1$ | 50 | 60 | 400 | 40 | 65 | 200 | 118 | 466 | ηatm. | 46.1 | 69.7 | 32.1 |
| 4 | Isobutane $Sb_{4.5}U_1$ | 80 | 100 | 600 | 64 | 65 | 250 | 118 | 485 | ηatm. | 52.9 | 61.4 | 32.5 |

TABLE 2

Effect of Molecular Ratio in Sb/Fe/U/W Catalyst

| | Catalyst Comp. | | | | Results after 100 cycles | | Results after 200 cycles | | Results after 1000 cycles | |
|---|---|---|---|---|---|---|---|---|---|---|
| | Sb | Fe | U | W | Conv. | Sel. to AN | Conv. | Sel. to AN | Conv. | Sel. to AN |
| Ex. 5 | 3 | 0.66 | 0.17 | 0.04 | 42 | 74 | 44 | 75 | 42 | 76 |
| Ex. 6 | 3 | 0.66 | 0.33 | 0.04 | 52 | 66 | 50 | 67 | 46 | 68 |
| Ex. 7 | 4 | 0.66 | 0.17 | 0.04 | 47 | 73 | 46 | 73 | 46 | 70 |
| Ex. 8 | 4 | 0.66 | 0.33 | 0.04 | 77 | 57 | N.C. | | N.C. | |
| C1 | 3 | 0.66 | — | 0.04 | 36 | 73 | 32 | 73 | N.C. | |
| C2 | 4 | 0.66 | — | 0.04 | 33 | 73 | 32 | 74 | N.C. | |
| C3 | 2 | 0.66 | — | 0.04 | 36 | 76 | 36 | 76 | 24 | 77 |

N.C. - Run not continued this far.

EXAMPLES 9–10

These Examples describe the performance of two catalysts in converting propane to acrylonitrile at a number of elapsed-time points from start-up. In each case the apparatus used is that described above. Example 10 shows also that the halogen promoter can be added to the catalyst in the regeneration zone.

EXAMPLE 9

| | |
|---|---|
| Catalyst used $Sb_{4.5}U_1$ | Temperature 488° C |
| Reaction zone feed | 80 scc/min propane |
| | 100 scc/min ammonia |
| | 64 scc/min 0.25% methyl bromide in nitrogen |
| Oxygenation zone feed | 600 scc/min air |
| First seal zone | 65 scc/min helium |
| Second seal zone | upper 250 scc/min helium |
| | lower 118 scc/min helium |

TABLE 3

| Time from Start | Propane Conversion | Selectivity to AN | SPAN |
|---|---|---|---|
| 1 hr. 30 min. | 40.6 | 67.8 | 27.5 |
| 2 hr. 25 min. | 37.6 | 70.5 | 26.5 |
| 3 hr. 30 min. | 39.4 | 68.1 | 26.8 |
| 4 hr. — | 34.3 | 70.0 | 24.0 |
| 4 hr. 40 min. | 37.8 | 68.6 | 25.9 |
| | average-37.9±2.3 | 69.0±1.1 | 26.1±1.3 |

EXAMPLE 9-continued (SPAN indicates single pass acrylonitrile conversion.)

EXAMPLE 10

| Catalyst used $Sb_6Fe_2U_1W_{0.12}$ | Temperature 479° C |
| --- | --- |
| Reaction zone feed | 80scc/min propane |
| | 100 scc/min ammonia |
| Oxygenation zone feed | 600 scc/min air |
| | 64 scc/min 0.5% methyl bromide in nitrogen |
| First seal zone | 220 scc/min helium |
| Second seal zone | upper 250 scc/min helium |
| | lower 120 scc/min helium |

TABLE 4

| Time from Start | Propane Conversion | Selectivity to AN | SPAN |
| --- | --- | --- | --- |
| 1 hr. 20 min. | 43.7 | 80.6 | 35.2 |
| 2 hr. 5 min. | 37.3 | 82.9 | 30.9 |
| 2 hr. 50 min. | 39.7 | 83.9 | 33.3 |
| 3 hr. 30 min. | 44.5 | 83.0 | 36.9 |
| 4 hr. 5 min. | 38.7 | 80.8 | 31.3 |
| | average-40.8±3.0 | 82.2±1.4 | 33.5±2.4 |

(SPAN indicates single pass acrylonitrile conversion.)

It is clear from the above Examples that the process of the invention affords an effective route for the conversion of propane and isobutane to acrylonitrile and methacrylonitrile respectively.

Further modifications of the process of the invention will be obvious to the man skilled in the art and it is intended that all such modifications as might reasonably be said to fall within the scope of the claims are included herein.

What is claimed is:

1. A process for the ammoxidation of a $C_3$–$C_5$ paraffin hydrocarbon to the corresponding unsaturated nitrile which comprises reacting the paraffin hydrocarbon with ammonia and oxygen at a temperature of from 350° to 550° C in the presence of a catalyst having the empirical formula $Sb_aU_bFe_cW_dO_e$ wherein $a$ is 1 to 10, $b$ is 0.01 to 1, $c$ is 0 to 1, $d$ is 0 to 0.1 and $e$ is a number chosen to satisfy the valencies of the other elements in the oxygenation states in which they appear characterized in that the catalysts has previously been oxygenated by heating in a molecular-oxygen containing gas and the oxygen required by the ammoxidation reaction is provided entirely by the oxygenated catalyst.

2. A process for the ammoxidation of a $C_3$–$C_5$ paraffin hydrocarbon to the corresponding unsaturated nitrile which comprises:
   a. passing a molecular oxygen-containing gas through a fluidized bed of a catalyst in an oxygenation zone, said catalyst having the empirical formula $Sb_aU_bFe_cW_dO_e$, wherein $a$ is 1 to 10, $b$ is 0.01 to 1, $c$ is 0 to 1, $d$ is 0 to 0.1 and $e$ is a number chosen to satisfy the valencies of the other elements in the oxidation states in which they appear, so as to oxygenate the catalyst;
   b. continuously forwarding oxygenated catalyst in a fluidized state to a reaction zone and, in said reaction zone, contacting said oxygenated catalyst in the fluidized state with $C_3$ to $C_5$ paraffin hydrocarbon and ammonia such that the paraffin hydrocarbon and ammonia react with oxygen from the oxygenated catalyst, at a temperature of from 350 to 550° C to produce the corresponding unsaturated nitrile, the oxygenated catalyst providing the only source of oxygen introduced into the reaction zone; and
   c. continuously removing catalyst from which oxygen has been removed from the reaction zone and transporting it in a fluidized state to the oxygenation zone.

3. A process according to claim 2 in which the paraffin hydrocarbon is selected from propane and isobutane.

4. A process according to claim 2 in which the reaction zone is maintained at a temperature of from 450° to 525° C and at substantially atmospheric pressure.

5. A process according to claim 2 in which the paraffin hydrocarbon is ammoxidized in the reaction zone in the presence of a halogen promoter which is an elemental halogen or a volatile halogen-containing compound.

6. A process according to claim 5 in which the halogen promoter is contacted with the catalyst in the oxygenation zone or in the reaction zone.

7. A process according to claim 5 in which the halogen in the halogen promoter is bromine.

8. A process according to claim 5 in which the halogen promoter is a $c_1$ to $c_3$ alkyl halide, an ammonium halide or a hydrogen halide.

9. A process for the ammoxidation of propane to acrylonitrile which comprises:
   a. passing air through a fluidized bed of a catalyst in an oxygenation zone, said catalyst having the empirical formula $Sb_aU_bFe_cW_dO_e$, wherein $a$ is 1 to 10, $b$ is 0.01 to 1, $c$ is 0 to 1, $d$ is 0 to 0.1 and $e$ is a number chosen to satisfy the valencies of the other elements in the oxidation states in which they appear, so as to oxygenate the catalyst;
   b. continuously forwarding oxygenated catalyst in a fluidized state to a fluidized catalyst bed in a reaction zone and, in said reaction zone, reacting propane with ammonia and oxygen given up by the catalyst, at a temperature of from 480° to 520° C in the presence of a halogen promoter selected from the group consisting of methyl bromide, ammonium bromide and hydrogen bromide, to produce acrylonitrile, the oxygenated catalyst providing the only source of oxygen introduced into the reaction zone; and c. continuously removing catalyst from which oxygen has been removed from the reaction zone and transporting it in a fluidized state to the oxygenation zone.

10. A process for the ammoxidation of isobutane to methacrylonitrile which comprises;

a. passing air through a fluidized bed of a catalyst in an oxygenation zone, said catalyst having the empirical formula $Sb_aU_bFe_cW_dO_e$, wherein $a$ is 1 to 10, $b$ is 0.01 to 1, $c$ is 0 to 1, $d$ is 0 to 0.1 and $e$ is a number chosen to satisfy the valencies of the other elements in the oxidation states in which they appear, so as to oxygenate the catalyst;

b. continuously forwarding oxygenated catalyst in a fluidized state to a fluidized catalyst bed in a reaction zone and, in said reaction zone reacting isobutane with ammonia and oxygen given up by the catalyst, at a temperature of from 450° to 525° C. in the presence of a halogen promoter selected from the group consisting of methyl bromide, ammonium bromide and hydrogen bromide, to produce methacrylonitrile, the oxygenated catalyst providing the only source of oxygen introduced into the reaction zone; and c. continuously removing catalyst from which oxygen has been removed from the reaction zone and transporting it in a fluidized state to the oxygenation zone.

* * * * *